United States Patent [19]

Timmler et al.

[11] 4,049,418
[45] Sept. 20, 1977

[54] METHOD OF REGULATING PLANT GROWTH

[75] Inventors: Helmut Timmler; Wilfried Draber; Karl Heinz Büchel, all of Wuppertal; Klaus Lürssen, Grosskoenigsdorf, all of Germany

[73] Assignee: Bayer Aktiengesellschaft, Leverkusen, Germany

[21] Appl. No.: 614,987

[22] Filed: Sept. 19, 1975

[30] Foreign Application Priority Data

Oct. 9, 1974    Germany ............................. 2448060

[51] Int. Cl.$^2$ ............................................. A01N 9/22
[52] U.S. Cl. ............................................. 71/76; 71/74; 74/92; 260/308 R; 260/308 A; 424/269; 548/341; 548/345; 548/378
[58] Field of Search ............................. 71/92, 76, 74

[56] References Cited

U.S. PATENT DOCUMENTS

| 3,754,001 | 8/1973 | Timmler et al. ..................... 71/92 X |
| 3,917,477 | 11/1975 | Hashimoto et al. .................... 71/76 |

FOREIGN PATENT DOCUMENTS

| 1,811,654 | 6/1970 | Germany |
| 2,053,080 | 5/1972 | Germany |

*Primary Examiner*—Lewis Gotts
*Assistant Examiner*—Catherine L. Mills
*Attorney, Agent, or Firm*—Burgess, Dinklage & Sprung

[57] ABSTRACT

Plant growth is regulated, e.g., inhibited or stimulated, by application to the plants or their habitat of effective amounts of at least one 5-azolyl-[a,d]-dibenzocycloheptene compound of the formula (I)

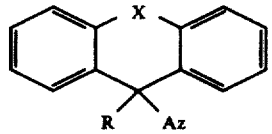

wherein
X is a —CH=CH— or —CH$_2$—CH$_2$— group,
R is alkyl, alkoxycarbonyl or optionally substituted aryl, and
Az is an azole radical of the formula

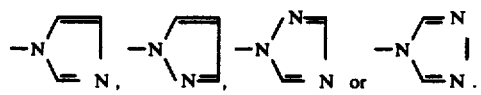

21 Claims, No Drawings

METHOD OF REGULATING PLANT GROWTH

The present invention relates to methods for regulating plant growth employing certain 5-azolyl-[a,d]-dibenzocycloheptene compounds.

It is known that certain 5-azolyl-[a,d]-dibenzocycloheptene derivatives exhibit activity against plant-pathogenic fungi and yeasts and in addition exhibit powerful antimycotic properties, from German Offenlegungsschriften (German Published Specifications) No. 1,811,654 and 2,053,080.

Furthermore, it is known that certain 2-halogenoethyltrialkylammonium halides exhibit plant growth-regulating properties (see U.S. Pat. No. 3,156,544). Thus, for example, an influence on plant growth, and especially an inhibition of vegetative plant growth in cereals and other crop plants, can be achieved by means of (2-chloroethyl)-trimethylammonium chloride (see U.S. Pat. Nos. 3,318,910; 3,280,136; 3,264,317 and 3,270,027). The action of this compound is however not always entirely satisfactory, especially if low amounts and low concentrations are used.

It has now been found that the 5-azolyl-[a,d]-dibenzocycloheptene derivatives of the general formula

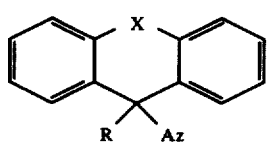

(I)

in which

X is a —CH=CH— or —CH$_2$—CH$_2$— group,
R is alkyl, alkoxycarbonyl or optionally substituted aryl, and
Az is an azole radical of the formula

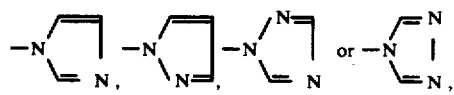

exhibit powerful plant growth-regulating properties.

Thus, the present invention provides a method of regulating the growth of plants, which comprises applying to the plants or to a habitat thereof a compound of the general formula (I) alone or in admixture with a diluent or carrier.

Preferably, R is straight-chain or branched alkyl of from 1 to 4 carbon atoms, alkoxycarbonyl of from 1 to 4 carbon atoms in alkyl part, or aryl of from 6 to 10 (especially of from 6) carbon atoms, which aryl radical can optionally carry one or more (preferably 1 to 3, and especially 1 or 2) identical or different substituents, preferred substituents being selected from straight-chain or branched alkyl of from 1 to 4 carbon atoms, halogen (especially chlorine and bromine) and halogenoalkyl of from 1 or 2 carbon atoms and of from 2 to 5 halogen atoms (the halogen atoms being preferably fluorine and/or chlorine, with trifluoromethyl requiring special mention as a suitable substituent) and Az is an imidazolyl-(1), 1,2,4-triazolyl-(1) or 1,3,4-triazolyl-(1) radical.

Surprisingly, the 5-azolyl-[a,d]-dibenzocycloheptene derivatives according to the invention show a greater plant growth-regulating action than (2-chloroethyl)-trimethylammonium chloride, known from the state of the art, which is recognized to be a compound of good activity, and of the same type of activity. The compounds which can be used according to the invention thus represent a valuable enrichment of the art.

The following may be mentioned as examples of the active compounds which can be used according to the invention: 5-ethyl-5-[imidazolyl-(1)]-[a,d]-dibenzocycloheptene, 5-iso-propyl-5-[1,2,4-triazolyl-(1)]-[a,d]-dibenzocycloheptene, 5-tert-butoxycarbonyl-5-[imidazolyl-(1)]-[a,d]-dibenzocycloheptene, 5-phenyl-5-[1,3,4-triazolyl-(1)]-[a,d]-dibenzocycloheptene, 5-(2-chlorophenyl)-5-[imidazolyl-(1)]-[a,d]-dibenzocycloheptene, 5-(4-bromophenyl)-5-[1,2,4-triazolyl-(1)]-[a,d]-dibenzocycloheptene, 5-(3-ethylphenyl)-5-[1,3,4-triazolyl-(1)]-[a,d]-dibenzocycloheptene, 5-(2,4-dimethylphenyl)-5-[imidazolyl-(1)]-[a,d]-dibenzocycloheptene, 5-(2-chloro-3-methylphenyl)-5-[1,2,4-triazolyl-(1)]-[a,d]-dibenzocycloheptene, 5-(4-trifluoromethylphenyl)-5-[imidazolyl-(1)]-[a,d]-dibenzocycloheptene, 10,11-dihydro-5-(4-trifluoromethylphenyl)-5-[imidazolyl-(1)]-[a,d]-dibenzocycloheptene, 10,11-dihydro-5-ethyl-5-[imidazolyl-(1)]-[a,d]-dibenzocycloheptene, 10,11-dihydro-5-iso-propyl-5-[1,2,4-triazolyl-(1)]-[a,d]-dibenzocycloheptene, 10,11-dihydro-5-tert-butoxycarbonyl-5-[imidazolyl-(1)]-[a,d]-dibenzocycloheptene, 10,11-dihydro-5-phenyl-5-[1,3,4-triazolyl-(1)]-[a,d]-dibenzocycloheptene, 10,11-dihydro-5-(2-chlorophenyl)-5-[imidazolyl-(1)]-[a,d]-dibenzocycloheptene, 10,11-dihydro-5-(4-bromophenyl)-5-[1,2,4-triazolyl-(1)]-[a,d]-dibenzocycloheptene, 10,11-dihydro-5-(3-ethylphenyl)-5-[1,3,4-triazolyl-(1)]-[a d]-dibenzocycloheptene, 10,11-dihydro-5-(2,4-dimethylphenyl)-5-[imidazolyl-(1)]-[a,d]-dibenzocycloheptene, 10,11-dihydro-5-(2-chloro-3-methylphenyl)-5-[1,2,4-triazolyl-(1)]-[a,d]-dibenzocycloheptene, 10,11-dihydro-5-methyl-5-[1,2,4-triazolyl-(1)-[a,d]-dibenzocycloheptene, 10,11-dihydro-5-ethyl-5-[pyrazolyl-(1)]-[a,d]-dibenzocycloheptene, 10,11-dihydro-5-n-propyl-5-[imidazolyl-(1)]-[a,d]-dibenzocycloheptene, 10,11-dihydro-5-ethoxycarbonyl-5-[1,3,4-triazolyl-(1)]-[a,d]-dibenzocycloheptene, 10,11-dihydro-5-methoxycarbonyl-5-[pyrazolyl-(1)]-[a,d]-dibenzocycloheptene, 10,11-dihydro-5-phenyl-5-[imidazolyl-(1)]-[a,d]-dibenzocycloheptene, 10,11-dihydro-5-phenyl-5-[pyrazolyl-(1)]-[a,d]-dibenzocycloheptene, 10,11-dihydro-5-(3-chlorophenyl)-5-[1,2,4-triazolyl-(1)]-[a,d]-dibenzocycloheptene and 10,11-dihydro-5-(2,4-dichlorophenyl)-5-[pyrazolyl-(1)]-[a,d]-dibenzocycloheptene.

Some of the compounds which can be used according to the invention are known from German Offenlegungsschriften (German Published Specifications) Nos. 1,811,654; 2,009,020 and 2,053,050. However, their use as plant growth regulators is new.

The compounds which can be used according to the invention but which have not been described in the literature can, however, be prepared in a simple manner in accordance with known processes. For example, they are obtained when 5-hydroxy-[a,d]-dibenzocycloheptene derivatives of the general formula (II)

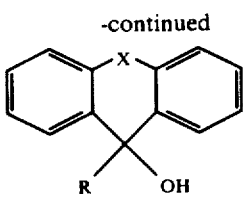

in which

X and R have the above-mentioned meanings, are reacted with thionyl-bis-azoles of the formula

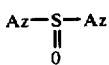
(III)

in which

Az has the above-mentioned meaning, if appropriate in the presence of a diluent (see the preparative example hereinafter).

The 5-hydroxy-[a,d]-dibenzocycloheptene derivatives of the formula (II), to be used as starting materials, are largely known from German Offenlegungsschriften (German Published Specifications) Nos. 1,811,654; 2,009,020 and 2,053,080, U.S. Pat. No. 3,406,186 and Chem. Ber. 83, 367-371 (1950) and Chem. Ber. 84, 671-679 (1951). The compounds of the formula (II) which were not previously known can be prepared in a simple manner in accordance with processes which have previously been described in the literature.

The thionyl-bis-azoles of the formula (III) required as reactants are also already known (see Angew. Chem. 73, 26 (1961) and Angew. Chem. 74, 407 (1962

Diluents which can be used in carrying out the reaction are preferably polar organic solvents, especially nitriles, such as acetonitrile; sulfoxides, such as dimethylsulfoxide; formamides, such as dimethylformamide; ketones, such as acetone; ethers, such as diethyl ether and tetrahydrofuran; and chlorohydrocarbons, such as methylene chloride and chloroform.

The reaction temperatures can be varied within a fairly wide range. In general, the reaction is carried out at between 0° C and 100° C, preferably between 20° C and 85° C. In the presence of a solvent, the reaction is suitably carried out at the boiling point of the particular solvent.

In carrying out the process, preferably 1 to 2 moles of the thionyl-bis-azole of the formula (III) are employed per mole of the 5-hydroxy-[a,d]-dibenzocycloheptene derivative of the formula (II). In a particular variant, the thionyl-bis-azole of the formula (III) required for the reaction can also be produced in situ. The reaction products are isolated in accordance with generally customary methods. A suitable procedure is to distill off any solvent present after completion of the reaction, digest the remaining residue with water and take it up in a suitable water-immiscible solvent, and then separate off, dry and concentrate the organic phase. The product which hereupon remains can, if appropriate, be purified by recrystallization.

The active compounds which can be used according to the invention participate in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegatative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit — for example in the case of table fruit — in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out completely mechanical or manual harvesting in only a single pass, for example in the case of tobacco, tomatoes or coffee.

By using growth regulators it is also possible to influence the latent period of seeds or buds of plants, that is to say that endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds to be used according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellents, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground synthetic minerals, such as highly dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds, such as fungicides, insecticides, acaricides and herbicides, and also as a mixture with fertilizers.

The formulations in general contain from 0.1 to 95 percent by weight of active compound, preferably from 0.5 to 90 percent by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in customary manner, for example by watering, spraying atomizing, scattering, dusting, foaming, gassing and the like. Furthermore it is possible to apply the active compounds in accordance with the ultra-low-volume (ULV) method, to spread the active compound preparation or the active compound itself on plants or parts of plants or to inject the active compound preparation or the active compound itself into the soil. It is also possible to treat the seeds of plants.

The active-compound concentrations can be varied within a fairly wide range. In general, concentrations of 0.00005 to 2%, preferably of 0.0001 to 0.5%, by weight are used. Furthermore, in general 0.01 to 50 kg. preferably 0.05 to 10 kg, of active compound are employed per hectare of soil area.

The preferred time of application of the growth regulators depends on the climatic and vegetative circumstances.

The present invention also provides crop plants, the growth of which has been regulated by their being grown in areas in which immediately prior to and/or during the time of the growing a compound of the formula (I) was applied, alone or in admixture with a diluent or carrier.

The compounds (I) not only have very good plant growth-regulating properties but also possess microbicidal, insecticidal, herbicidal, bactericidal and fungicidal activity. The fungicidal activity is in particular directed against powdery mildew fungi and — if the material is used as a dressing-against Helminthosporium.

The biotest examples which follow show the activity of the compounds (I) as growth regulators without excluding the possibility of further applications as growth regulators.

Example A

Influence on growth of barley

Solvent:10 parts by weight of methanol
Emulsifier:2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young barley plants, 5-8 cm high, were sprayed with the preparation of active compound until dripping wet. After 14 days, the additional growth was measured and the influence on the growth, in % of the additional growth of the control plants, was calculated. 0% denotes growth corresponding to that of the control plants. Positive values characterize a promotion of growth compared to the control plants whilst negative values correspondingly indicate an inhibition of growth.

Table A

| | Influence on growth of barley | |
|---|---|---|
| Active compound | Active compound concentration in % | Influence on growth in % of the additional growth of the control plants |
| -(control) | — | 0 |
| Cl—CH$_2$—CH$_2$—$\overset{\oplus}{N}$(CH$_3$)$_3$Cl$^\ominus$ (known) | 0.05 | −10 |
| | 0.10 | +10 |
| (2) | | |

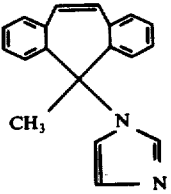

Example B

Influence on growth of grass (Festuca pratensis)

Solvent: 10 parts by weight of methanol
Emulsifier: 2 parts by weight of polyethylene sorbitan monolaurate To prepare a suitable preparation of active compound, 1 part of weight of active compound was mixed with the stated amounts of solvent and emulsifier and the mixture was made up to the desired concentration with water.

3 to 4 cm high grass plants (Festuca pratensis) were sprayed with the preparations of active compound until dripping wet. After 14 days, the additional growth was measured and the influence on the growth, in % of the additional growth of the control plants, was calculated. 0% denotes growth corresponding to that of the control plants. Positive values characterize a promotion of growth compared to the control plants whilst negative values correspondingly indicate an inhibition of growth.

The active compounds, active-compound concentrations and results can be seen from the table which follows:

Table B

| | Influence on growth of grass (Festuca pratensis) | |
|---|---|---|
| Active Compound | Active compound concentration in % | Influence on growth in % of the additional growth of the control plants |
| -(control) | — | 0 |
| (structure) | 0.02 | +15 |
| | 0.05 | +15 |
| (4) | 0.02 | +15 |
| (structure) | 0.05 | +20 |
| (2) | | |

Example C

Inhibition of growth of cress seedlings

Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

50 cress seeds at a time were laid on a stiff filter paper which has been cut to a rectangular shape and was impregnated with an 0.02% strength solution of the particular prepparation of active compound. The seeds adhered sufficiently firmly to the moist filter paper that they did not fall off when the paper was stood upright. The moist filter paper loden with seeds was stood upright in a beaker (capacity 250 ml) which contained 20 ml of the particular 0.02% strength solution of active compound. The beaker was covered with a glass plate. After 4 days, the length of the seedlings was measured and the inhibition of growth compared to the control plants was expressed in %. 100% denotes cessation of growth and 0% denotes a growth which corresponded to that of control plants.

The control plants were treated with distilled water which contains an amount of solvent and emulsifier corresponding to the preparations of active compound.

The active compounds, active compound concentrations and results can be seen from the table which follows:

Table C

| | Inhibition of growth of cress seedlings | | |
|---|---|---|---|
| Active compound | Active compound concentration in % | Inhibition of growth in % of the control | Notes |
| -(control) | — | 0 | — |
| Cl—CH$_2$—CH$_2$—N$^\oplus$(CH$_3$)$_3$Cl$^\ominus$ (known) | 0.02 | 5 | — |

Table C-continued

| Active compound | Inhibition of growth of cress seedlings | | Notes |
|---|---|---|---|
| | Active compound concentration in % | Inhibition of growth in % of the control | |
| (structure with CH₃OOC and imidazolyl) (1) | 0.02 | 65 | — |
| (structure with CH₃ and imidazolyl) (4) | 0.02 | 65 | dark green leaves |
| (structure with CH₃ and imidazolyl) (2) | 0.02 | 62 | dark green leaves |

The following examples illustrate the preparation of compounds used in the invention.

Example 1

Preparation of 10,11-dihydro-5-[imidazolyl-(1)]-5-methoxycarbonyl-[a,d]-dibenzocycloheptene

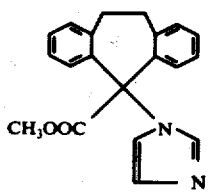

(1)

8.04 g (0.03 mole) of 10,11-dihydro-5-hydroxy-5-methoxycarbonyl-[a,d]-dibenzocycloheptene were dissolved in 50 ml of acetonitrile and a solution of 0.05 mole of thionyl-bis-imidazole in 50 ml of acetonitrile was added. After prolonged standing at room temperature, the mixture was heated to the boil for about 3 hours, whilst stirring. The solvent was then distilled off and the residue was digested with water and extracted by shaking with ether. The ether phase was dried over sodium sulfate. After distilling off the ether, the residue was recrystallized from ligroin/ethyl acetate (1:1). 8 g (83% of theory) of 10,11-dihydro-5-[imidazolyl-(1)]-5-methoxycarbonyl-[a,d]-dibenzocycloheptene of melting point 155° C were obtained.

10,11-Dihydro-5-hydroxy-5-methoxycarbonyl-[a,d]-dibenzocycloheptene, used as the starting material, was prepared according to the teaching of U.S. Pat. No. 3,406,186.

Example 2

Preparation of 5-[imidazolyl-(1)]-5-methyl-[a,d]-dibenzocycloheptene

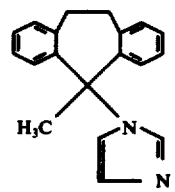

(2)

22.2 g (0.1 mole) of 5-hydroxy-5-methyl-[a,d]-dibenzocycloheptene were dissolved in 300 ml of acetonitrile and a solution of 0.15 mole of thionyl-bis-imidazole in 200 ml of acetonitrile was added. After prolonged standing at room temperature, the mixture was heated to the boil for about 3 hours, while stirring. The solvent was then distilled off and the residue was digested with water and extracted by shaking with ether. The ether phase was dried over sodium sulfate. After distilling off the ether, 15 g (56% of theory) of 5-[imidazolyl-(1)]-5-methyl-[a,d]-dibenzocycloheptene of melting point 188° C were obtained.

5-Hydroxy-5-methyl-[a,d]-dibenzocycloheptene, used as the starting material, was prepared according to the instructions of W. Treibs and H. J. Klinkhammer, Chem. Ber. 84, 671–679 (1951).

The compounds listed in Table 1 which follows were obtained by methods analogous to those described in Examples 1 and 2.

Table 1

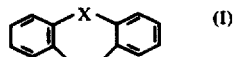

| Example No. | X | R | Az | Melting point (° C) |
|---|---|---|---|---|
| 3 | —CH$_2$—CH$_2$— | C$_6$H$_5$ | Imidazolyl-(1) | 186–187 |
| 4 | —CH$_2$—CH$_2$— | CH$_3$ | Imidazolyl-(1) | 158–159 |
| 5 | —CH$_2$—CH$_2$— | 4-Cl-C$_6$H$_4$ | 1,2,4-Triazolyl-(1) + isomer | 117–180 |
| 6 | —CH=CH— | 4-Cl-C$_6$H$_4$ | Imidazolyl-(1) | 231 |

It will be understood that the foregoing specification and examples are illustrative but not limitative of the present invention inasmuch as other embodiments within the spirit and scope of the invention will suggest themselves to those skilled in the art.

What is claimed is:

1. A method of regulating the growth of plants, which comprises applying to the plants or a habitat thereof an effective amount of a 5-azolyl-[a,d]-dibenzocycloheptene compound of the formula

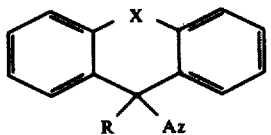

in which
X is a —CH=CH— or CH$_2$—CH$_2$— group,
R is alkyl of from 1 to 4 carbon atoms, alkoxycarbonyl of from 1 to 4 carbon atoms in the alkyl moiety, or phenyl, wherein the phenyl radical may be substituted by up to 3 substituents selected from alkyl of from 1 to 4 carbon atoms, halogen, haloalkyl of up to 2 carbon atoms and up to 5 carbon atoms and
Az is an azole radical selected from the formulas

2. Method as claimed in claim 1 wherein X in the formula is a —CH=CH— group.
3. Method as claimed in claim 1 wherein X in the formula is a —CH$_2$—CH$_2$— group.
4. Method as claimed in claim 1 wherein R in the formula is alkyl of from 1 to 4 carbon atoms.
5. Method as claimed in claim 1 wherein R in the formula is alkoxycarbonyl of from 1 to 4 carbon atoms in the alkoxy moiety.
6. Method as claimed in claim 1 wherein R in the formula is aryl of from 6 to 10 carbon atoms.
7. Method as claimed in claim 1 wherein R in the formula is aryl substituted with at least one of alkyl or haloalkyl of up to 4 carbon atoms and halogen.
8. Method as claimed in claim 1 wherein R in the formula is aryl substituted with trifluormethyl.

9. Method as claimed in claim 1 wherein Az in the formula is an azole radical of the formula

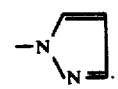

10. Method as claimed in claim 1 wherein Az in the formula is an azole radical of the formula

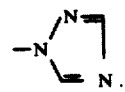

11. Method as claimed in claim 1 wherein Az in the formula is an azole radical of the formula

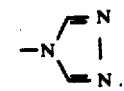

12. Method as claimed in claim 1 wherein Az in the formula is an azole radical of the formula 13. Method as claimed in claim 1 wherein the compound is 10,11-dihydro-5-[imidazolyl-(1)]-5-methoxycarbonyl-[a,d]-dibenzocycloheptene.
14. Method as claimed in claim 1 wherein the compound is 5-[imidazolyl-(1)]-5-methyl-[a,d]-dibenzocycloheptene.
15. Method as claimed in claim 1 wherein the compound is 10,11-dihydro-5-[imidazolyl-(1)]-5-methyl-[a,d]-dibenzocycloheptene.
16. Method as claimed in claim 1 wherein the growth of the plant is stimulated by applying amounts of said compound effective for stimulating plant growth.
17. Method as claimed in claim 1 wherein the growth of the plant is inhibited by the application of an amount of compound effective to inhibit plant growth.
18. Method as claimed in claim 1 wherein the growth of plant is altered by applying said compound in sufficient amount of alter plant growth.
19. Method as claimed in claim 16 wherein the plant is barley.
20. Method as claimed in claim 16 wherein the plant is a grass.
21. Method as claimed in claim 17 wherein the plant is cress.